(12) United States Patent
Torgerson

(10) Patent No.: US 8,219,196 B2
(45) Date of Patent: Jul. 10, 2012

(54) DETERMINATION OF STIMULATION OUTPUT CAPABILITIES THROUGHOUT POWER SOURCE VOLTAGE RANGE

(75) Inventor: Nathan A. Torgerson, Andover, MN (US)

(73) Assignee: Medtronic, Inc., Minneapolis, MN (US)

(*) Notice: Subject to any disclaimer, the term of this patent is extended or adjusted under 35 U.S.C. 154(b) by 337 days.

(21) Appl. No.: 12/362,167

(22) Filed: Jan. 29, 2009

(65) Prior Publication Data

US 2010/0114257 A1    May 6, 2010

Related U.S. Application Data

(60) Provisional application No. 61/110,448, filed on Oct. 31, 2008.

(51) Int. Cl.
*A61N 1/00* (2006.01)

(52) U.S. Cl. .............. 607/27; 607/30; 607/31; 607/32; 607/33; 607/60; 607/61; 607/62; 607/116

(58) Field of Classification Search .................. 607/27, 607/30–33, 60–62, 116
See application file for complete search history.

(56) References Cited

U.S. PATENT DOCUMENTS

| | | | |
|---|---|---|---|
| 4,476,869 A | 10/1984 | Bihn | |
| 4,606,350 A | 8/1986 | Frost | |
| 4,830,005 A | 5/1989 | Woskow | |
| 5,065,083 A | 11/1991 | Owens | |
| 5,453,698 A | 9/1995 | Williams et al. | |
| 5,744,931 A | 4/1998 | Arai et al. | |
| 6,023,641 A | 2/2000 | Thompson | |
| 6,115,272 A | 9/2000 | Pasternak | |
| 6,748,273 B1 | 6/2004 | Obel et al. | |
| 6,799,070 B2 | 9/2004 | Wolfe et al. | |

(Continued)

FOREIGN PATENT DOCUMENTS

WO    WO 00/43065    7/2000

(Continued)

OTHER PUBLICATIONS

Final office action for U.S. Appl. No. 11/943,858, dated Nov. 7, 2011, 11 pages.

(Continued)

*Primary Examiner* — Nicole F Lavert
(74) *Attorney, Agent, or Firm* — John W. Albrecht; Shumaker & Sieffert, P.A.

(57) ABSTRACT

Techniques for determining whether a medical device will be able to deliver stimulation according to a particular program throughout a useable voltage range of a power source of the medical device are described. According to some examples, the medical device configures a DC to DC converter of the medical device in a specified output configuration and delivers electrical stimulation from the medical device according to a program while at the specified output configuration. Whether the medical device will be able to deliver stimulation according to the program when the power source is at a power source voltage level lower than a present voltage level used during therapy delivery is determined based on a value of a voltage drop across a regulator module determined while delivering the electrical stimulation according to the program. The determination for a program may be performed, as an example, when the program is created or modified.

19 Claims, 9 Drawing Sheets

U.S. PATENT DOCUMENTS

| | | |
|---|---|---|
| 6,871,090 B1 | 3/2005 | He et al. |
| 6,901,293 B2 | 5/2005 | Rogers et al. |
| 2003/0007373 A1 | 1/2003 | Satoh |
| 2003/0174078 A1 | 9/2003 | Ohlsson |
| 2003/0187485 A1 | 10/2003 | Sturman et al. |
| 2003/0204225 A1 | 10/2003 | Heathershaw et al. |
| 2004/0138724 A1 | 7/2004 | Sieracki et al. |
| 2004/0147983 A1 | 7/2004 | Czygan |
| 2004/0162592 A1 | 8/2004 | Betzold et al. |
| 2004/0167407 A1* | 8/2004 | Roberts .................. 600/485 |
| 2005/0180179 A1 | 8/2005 | Hirst |
| 2007/0135868 A1* | 6/2007 | Shi et al. .................. 607/62 |
| 2007/0156203 A1 | 7/2007 | Varrichio et al. |
| 2007/0179547 A1 | 8/2007 | Armstrong et al. |
| 2007/0191907 A1* | 8/2007 | Stein et al. .................. 607/46 |

FOREIGN PATENT DOCUMENTS

| | | |
|---|---|---|
| WO | WO 2006/029007 A2 | 3/2006 |
| WO | WO2008/036869 A1 | 3/2008 |

OTHER PUBLICATIONS

Response to final office action for U.S. Appl. No. 11/943,858, filed Jan. 9, 2012, 8 pages.

Patent Application entitled "Determination of Stimulation Output Capabilities Throughout Power Source Voltage Range," U.S. Appl. No. 11/943,858, filed Nov. 21, 2007, Torgerson.

Patent Application entitled "Determination of Stimulation Output Capabilities Throughout Power Source Voltage Range," U.S. Appl. No. 12/362,198, filed Jan. 29, 2009, Torgerson.

Office action for U.S. Appl. No. 11/943,858, mailed Jun. 8, 2011, 13 pages.

Response to office action for U.S. Appl. No. 11/943,858, filed Sep. 8, 2011, 21 pages.

Notification of Transmittal of the International Search Report and the Written Opinion of the International Searching Authority for corresponding patent application No. PCT/US2009/041544, mailed Oct. 21, 2009, 13 pages.

* cited by examiner

DETERMINATION OF STIMULATION OUTPUT CAPABILITIES THROUGHOUT POWER SOURCE VOLTAGE RANGE

This application claims the benefit of U.S. Provisional Application No. 61/110,448, filed Oct. 31, 2008, the entire content of which is incorporated herein by reference.

TECHNICAL FIELD

The invention relates to medical devices and, more particularly, to medical devices that include a power source and deliver electrical stimulation.

BACKGROUND

Medical devices may be used to treat a variety of medical conditions. Some medical devices are surgically implanted within the patient, while others are connected externally to the patient receiving treatment. Some medical devices receive electrical power from batteries, such as non-rechargeable primary cell batteries or rechargeable batteries, or another power source inside the medical device, such as a supercapacitor. An electrical stimulator is an example of a medical device that receives power from an internal source for delivery of a therapy to a patient.

Electrical stimulators may be used to deliver electrical stimulation therapy to patients to treat a variety of symptoms or conditions, such as chronic pain, tremor, Parkinson's disease, epilepsy, urinary or fecal incontinence, sexual dysfunction, obesity, or gastroparesis. An electrical stimulator may deliver stimulation therapy via leads that include electrodes located, as examples, proximate to the spinal cord, pelvic nerves, or stomach, on or within the brain, or within the pelvic floor. In general, the electrical stimulator delivers stimulation therapy in the form of electrical pulses or substantially continuous-time signals. The electrical stimulator may be external or implanted, for example, in a chest cavity, lower back, lower abdomen, or buttocks of a patient.

A clinician selects values for a number of programmable therapy parameters in order to define the stimulation therapy to be delivered to a patient. For example, the clinician may select an amplitude, which may be a current or voltage amplitude. When therapy is delivered in the form of electrical pulses, the clinician may also select a pulse width for a stimulation waveform to be delivered to the patient as well as a rate at which the pulses are to be delivered to the patient. The clinician may also select particular electrodes within an electrode set to be used to deliver the pulses or continuous-time signal, and the polarities of the selected electrodes. The selected electrodes and their polarities may be referred to as an electrode combination or configuration. A group of parameter values may be referred to as a program in the sense that they drive the electrical stimulation therapy to be delivered to the patient.

SUMMARY

In general, the invention is directed toward determining, for a given program, whether a medical device will be able to provide a stimulation output specified by the program throughout a voltage range of a power source of the medical device, e.g., throughout the life of a primary cell battery or between recharge cycles of a rechargeable power source, such as a rechargeable battery or supercapacitor. When the level of charge of a power source of a medical device depletes, the ability of the medical device to deliver adequate stimulation may be impacted. For example, in embodiments that use a voltage or current regulator for delivery of stimulation, decreased power source voltage may result in an out of regulation condition for a given program.

A medical device may deliver therapy according to a selected program using a maximum output configuration of a DC to DC converter. The voltage output from the DC to DC converter is input into a regulator module. When the maximum output configuration is used, the voltage output from the DC to DC converter and, consequently, the voltage input into the regulator module is as large as possible for the present voltage level of the power source. The regulator module receives the maximum voltage but outputs a lower voltage based on the program selected for therapy delivery. As the power source depletes, the total voltage output of the DC to DC converter decreases, and the DC to DC converter is not able to supply as much voltage to the regulator module.

Determining the voltage drop across the regulator module provides information regarding the relationship between the maximum voltage that the DC to DC converter can produce at the present voltage level of the power source and the output required by the selected program. A determination as to whether the medical device will be able to deliver stimulation according to the selected program at the power source voltage level lower than the present power source voltage level may be made based on the determined voltage drop across the regulator module. As one example, the lower power source voltage level may be a power source voltage level a rechargeable power source may have just prior to or otherwise near full depletion.

The determination may allow a user to alter one or more therapy parameters of the program to ensure that it will be properly delivered over a range of power source voltages. In some embodiments of the invention, a user is alerted when it is determined that the medical device will not be able to deliver stimulation according to the program when the power source is at the lower voltage level. These techniques for determining whether a medical device will be able to provide a stimulation output specified by the program throughout a voltage range of a power source of the medical device may be performed, as an example, when a program is created or modified.

In one embodiment, the invention is directed to a method comprising configuring a DC to DC converter of a medical device in a specified output configuration, delivering electrical stimulation from the medical device according to a program while at the specified output configuration, wherein delivering electrical stimulation comprises providing an output of the DC to DC converter to a regulator module within the medical device, determining a value of a voltage drop across the regulator module while delivering the electrical stimulation according to the program, and determining whether the medical device will be able to deliver stimulation according to the program at a power source voltage level lower than a present voltage level of a power source based on the determined value of the voltage drop.

In another embodiment, the invention is directed to a medical device comprising a power source at a present power source voltage level, a signal generator that generates electrical stimulation, wherein the signal generator comprises a DC to DC converter coupled to the power source and a regulator module coupled to the DC to DC converter, and a processor that controls the signal generator to configure the DC to DC converter in a specified output configuration and deliver stimulation according to a program while at the specified output configuration, determines a value of a voltage drop across the regulator module during the delivery of electrical stimulation according to the program, and determines whether the medical device will be able to deliver stimulation according to the program at a power source voltage level lower than the present voltage level of the power source based on the determined value of the voltage drop.

In another embodiment, the invention is directed to a system comprising an external programming device and an implantable medical device comprising a power source at a present power source voltage level, a DC to DC converter coupled to the power source, and a regulator module coupled to the DC to DC converter, wherein the implantable medical device configures the DC to DC converter in a specified output configuration, delivers electrical stimulation according to a program while at the specified output configuration, determines a value of a voltage drop across the regulator module during the delivery of electrical stimulation according to the program, determines whether the implantable medical device will be able to deliver stimulation according to the program at a power source voltage level lower than the present voltage level of the power source based on the determined value of the voltage drop, and transmits an indication of the determination of whether the implantable medical device will be able to deliver stimulation according to the program at the lower power source voltage level to the external programming device.

In yet another embodiment, the invention is directed to a medical device comprising means for configuring a DC to DC converter in a specified output configuration, means for delivering electrical stimulation according to a program while at the specified output configuration, means for determining a value of a voltage drop across a regulator module within the medical device while delivering the electrical stimulation according to the program, and means for determining whether the medical device will be able to deliver stimulation according to the program a power source voltage level lower than a present voltage level of a power source based on the determined value of the voltage drop.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
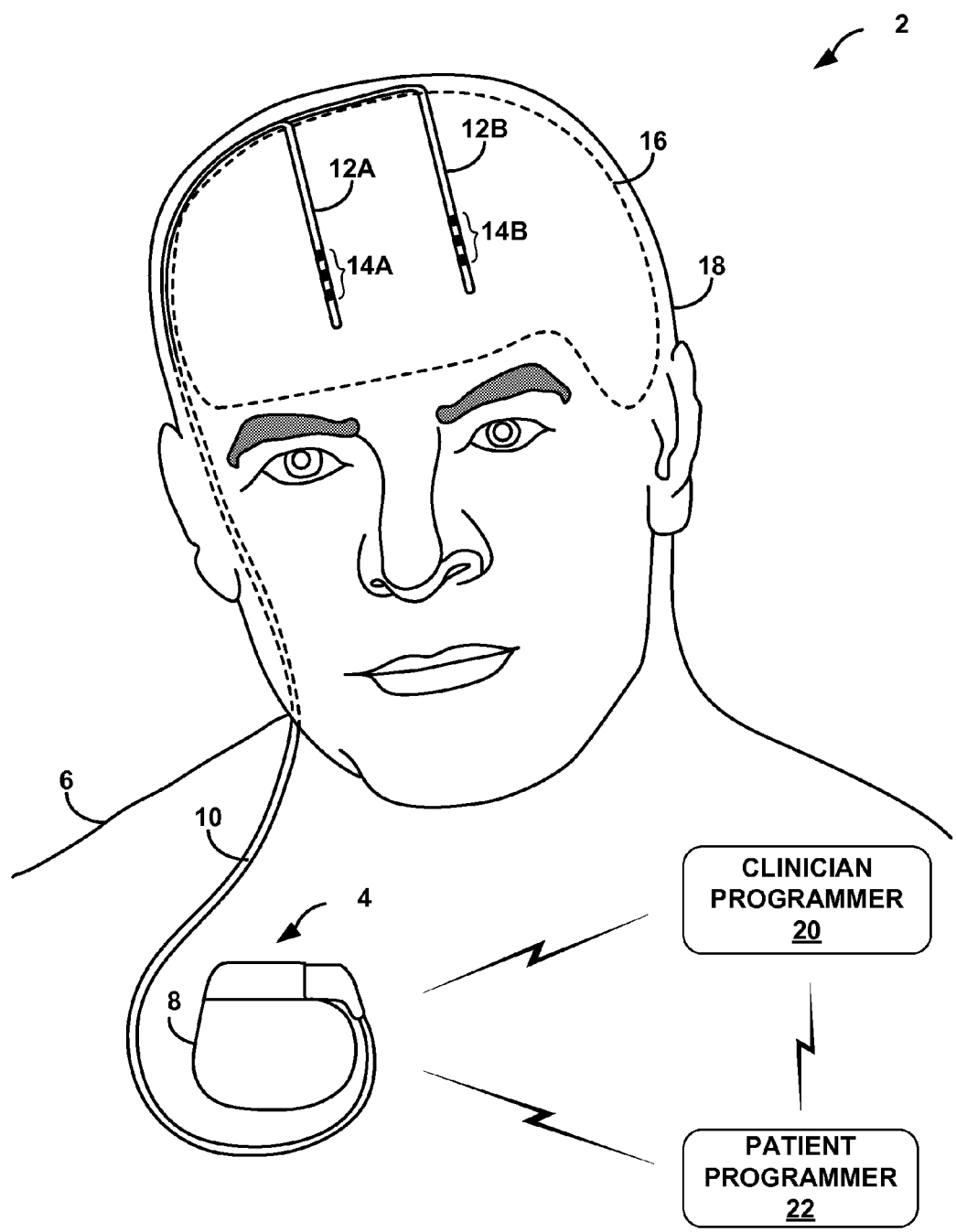
FIG. 1 is a schematic perspective view of an example therapy system, which includes an electrical stimulator coupled to a stimulation lead.

FIG. 1 is a schematic perspective view of therapy system 2, which includes a medical device 4. Medical device 4 may be either implantable or external. In the example of FIG. 1, medical device 4 has been implanted in patient 6. For example, medical device 4 may be subcutaneously implanted in the body of patient 6 (e.g., in a chest cavity, lower back, lower abdomen, buttocks, or cranium of patient 6). Patient 6 will ordinarily be a human patient. In some cases, however, the invention may be applied to a non-human patient.

In the embodiment illustrated in FIG. 1, medical device 4 is an electrical stimulator and provides a programmable stimulation signal (e.g., in the form of electrical pulses or substantially continuous-time signals) that is delivered to patient 6 by implantable medical lead 10 and, more particularly, via one or more stimulation electrodes carried by lead 10. Medical device 4 may also be referred to as a pulse or signal generator. In the example of FIG. 1, the distal end of lead 10 is bifurcated and includes two segments 12A and 12B. Segments 12A and 12B each include an electrode array 14A and 14B, respectively. At least some of the electrodes of arrays 14A and 14B may be stimulation electrodes to deliver a stimulation signal from medical device 4 to patient 6. In some embodiments, lead 10 may also carry one or more sense electrodes to permit electrical medical device 4 to sense electrical signals from patient 6. In various embodiments, medical device 4 may be coupled to one or more leads, which may or may not be bifurcated.

A proximal end of lead 10 may be both electrically and mechanically coupled to medical device 4 either directly or indirectly (e.g., via a lead extension). In particular, conductors disposed in the lead body may electrically connect stimulation electrodes adjacent to the distal end of lead 10 (e.g., the electrodes of electrode arrays 14A and 14B) to medical device 4.

In the example shown in FIG. 1, lead 10 extends to brain 16 of patient 6, e.g., through cranium 18 of patient 6. Medical device 4 may deliver deep brain stimulation (DBS) or cortical stimulation (CS) therapy to patient 6 via the electrodes of arrays 14A and 14B of lead 10 to treat any of a variety of movement disorders, including tremor, Parkinson's disease, spasticity, epilepsy, or dystonia. However, the invention is not limited to the configuration of lead 10 and electrodes arrays 14A and 14B shown in FIG. 1, or to the delivery of DBS or CS therapy.

Therapy system 2 may be useful in other stimulation applications, including pelvic floor stimulation, spinal cord stimulation, cortical surface stimulation, neuronal ganglion stimulation, gastric stimulation, peripheral nerve stimulation, or subcutaneous stimulation. Such therapy applications may be targeted to a variety of disorders such as chronic pain, peripheral vascular disease, angina, headache, tremor, depression, Parkinson's disease, epilepsy, urinary or fecal incontinence, sexual dysfunction, obesity, or gastroparesis. Further, therapy system 2 may be useful in non-neurostimulation contexts. For example, medical device 4 may be used to deliver stimulation to a target muscle tissue site via leads to, for example, provide functional electrical stimulation or cardiac stimulation, e.g., cardiac pacing. In various embodiments, therapy system 2 may deliver therapy to any nerve or other tissue site in patient 6.

Therapy system 2 also may include a clinician programmer 20 and a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation parameters, i.e., create programs, for use in delivery of stimulation therapy. Clinician programmer 20 may support telemetry (e.g., radio frequency telemetry) with medical device 4 to download programs and, optionally, upload operational or physiological data stored by medical device 4. In this manner, the clinician may periodically interrogate medical device 4 to evaluate efficacy and, if necessary, modify the programs or create new programs. In some embodiments, clinician programmer 20 transmits programs to patient programmer 22 in addition to or instead of medical device 4.

Like clinician programmer 20, patient programmer 22 may be a handheld computing device. Patient programmer 22 may also include a display and input keys to allow patient 6 to interact with patient programmer 22 and medical device 4. In this manner, patient programmer 22 provides patient 6 with a user interface for control of the stimulation therapy delivered by medical device 4. For example, patient 6 may use patient programmer 22 to start, stop or adjust electrical stimulation therapy. In particular, patient programmer 22 may permit patient 6 to adjust stimulation parameters of a program such as duration, current or voltage amplitude, pulse width and pulse rate. Patient 6 may also select a program, e.g., from among a plurality of stored programs, as the current program to control delivery of stimulation by medical device 4.

In some embodiments, medical device 4 delivers stimulation according to a group of programs at any given time. Each program of such a program group may include respective values for each of a plurality of therapy parameters, such as respective values for each of amplitude (e.g., current or voltage amplitude), pulse width, pulse rate and electrode combination. Medical device 4 may interleave pulses or other signals according to the different programs of a program group, e.g., cycle through the programs, to, for example, simultaneously treat different symptoms or provide a combined therapeutic effect. In such embodiments, clinician programmer 20 may be used to create programs, and assemble the programs into program groups. Patient programmer 22 may be used to adjust stimulation parameters of one or more programs of a program group, and select a program group, e.g., from among a plurality of stored program groups, as the current program group to control delivery of stimulation by medical device 4.

Medical device 4, clinician programmer 20, and patient programmer 22 may communicate via cables or a wireless communication, as shown in FIG. 1. Clinician programmer 20 and patient programmer 22 may, for example, communicate via wireless communication with medical device 4 using RF telemetry techniques known in the art. Clinician programmer 20 and patient programmer 22 also may communicate with each other using any of a variety of local wireless communication techniques, such as RF communication according to the 802.11 or Bluetooth specification sets, infrared communication, e.g., according to the IrDA standard, or other standard or proprietary telemetry protocols. Each of clinician programmer 20 and patient programmer 22 may include a transceiver to permit bi-directional communication with medical device 4.

Figure 2:
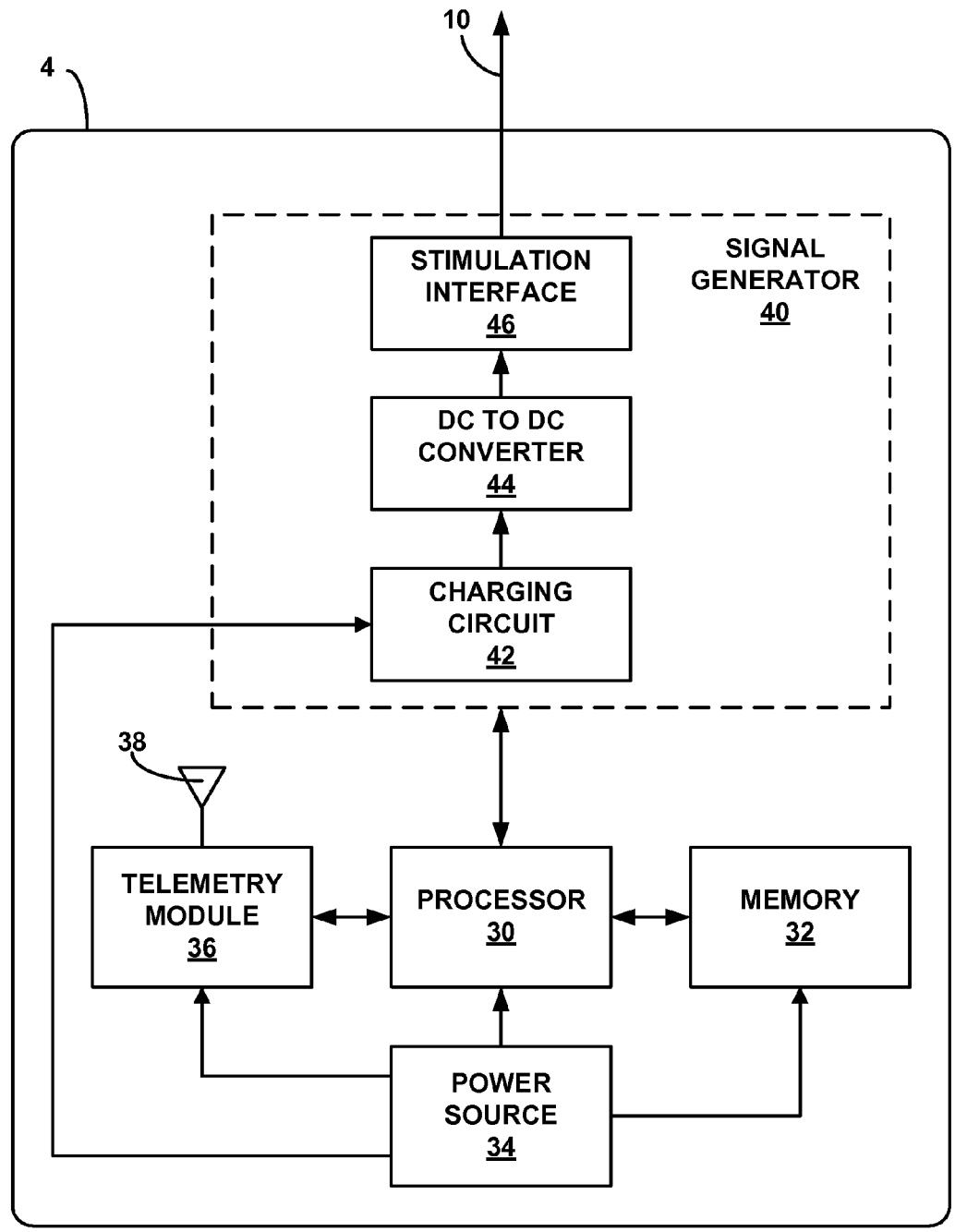
FIG. 2 is a block diagram illustrating various components of an example electrical stimulator.

FIG. 2 is a block diagram illustrating various components of medical device 4. In the example of FIG. 2, medical device 4 includes processor 30, memory 32, power source 34, telemetry module 36, antenna 38, and signal generator 40. Telemetry module 36 may permit communication with clinician programmer 20 and patient programmer 22 to receive, for example, new programs or program groups, or adjustments to programs or program groups.

Processor 30 may include one or more microprocessors, digital signal processors (DSPs), application-specific integrated circuits (ASICs), field-programmable gate arrays (FPGAs), or other digital logic circuitry. Processor 30 controls operation of medical device 4, e.g., controls signal generator 40 to deliver stimulation therapy according to a selected program or group. For example, processor 30 may control signal generator 40 to deliver electrical signals with current or voltage amplitudes, pulse widths (if applicable), and rates specified by one or more stimulation programs. Processor 30 may also control signal generator 40 to deliver the stimulation signals via subsets of the electrodes of arrays 14A and 14B with polarities, the subsets and polarities specified as electrode combinations or configurations by one or more programs.

At any given time, processor 30 may control signal generator 40 to deliver stimulation according to a selected one or more of a plurality of programs or program groups stored in memory 32. Memory 32 may include any magnetic, electronic, or optical media, such as random access memory (RAM), read-only memory (ROM), electronically-erasable programmable ROM (EEPROM), flash memory, or the like. Memory 32 may store program instructions that, when executed by processor 30, cause the processor to perform the functions ascribed to it and medical device 4 herein.

Telemetry module 36 may include a transceiver to permit bi-directional communication between medical device 4 and each of clinician programmer 20 and patient programmer 22. Telemetry module 36 may include an antenna 38 that may take on a variety of forms. For example, antenna 38 may be formed by a conductive coil or wire embedded in a housing associated with medical device 4. Alternatively, antenna 38 may be mounted on a circuit board carrying other components of electrical stimulator 4 or take the form of a circuit trace on the circuit board.

Power source 34 may be a non-rechargeable primary cell battery or a rechargeable battery and may be coupled to power circuitry. However, the invention is not limited to embodiments in which the power source is a battery. In another embodiment, as an example, power source 34 may comprise a supercapacitor. In some embodiments, power source 34 may be rechargeable via induction or ultrasonic energy transmission, and include an appropriate circuit for recovering transcutaneously received energy. For example, power source 34 may be coupled to a secondary coil and a rectifier circuit for inductive energy transfer.

Signal generator 40 produces an electrical stimulation signal in accordance with a program based on control signals from processor 30. As shown in FIG. 2, signal generator 40 may include a charging circuit 42, a DC to DC converter 44, and a stimulation interface 46. In the embodiment illustrated in FIG. 2, DC to DC converter 44 is a capacitor module and, therefore, may be referred to as capacitor module 44. Although DC to DC converter 44 is primarily described with respect to capacitor module 44, this disclosure is not limited to embodiments in which DC to DC converter 44 is a capacitor module. In other embodiments, DC to DC converter 44 may comprise, for example, an inductor-based charge pump, a capacitor-based charge pump, and/or any other type of DC to DC converter.

Charging circuit 42 selectively, e.g., based on signals from processor 30, applies energy from power source 34 to capacitor module 44 to charge the capacitor module for delivery of a stimulation signal, e.g., pulse. For delivery of pulses, charging circuit 42 may control the pulse rate based on signals from the processor by controlling the rate at which capacitor module 44 is recharged. In addition to capacitors, capacitor module 44 may include switches. In this manner, capacitor module 44 may be configurable, e.g., based on signals from processor 30, to store a desired voltage for delivery of stimulation at a voltage or current amplitude specified by a program. For delivery of stimulation pulses, switches within capacitor module 44 may control the width of the pulses based on signals from processor 30.

Stimulation interface 46 conditions charge from capacitor module 44 to produce an electrical stimulation signal, e.g., a pulse, under control of processor 30 for application to at least some electrodes of electrode arrays 14A and 14B carried by lead 10. Stimulation interface 46 may control the voltage or current amplitude of the signal based on signals from processor 30. Stimulation interface 46 may also control to which electrodes of arrays 14A and 14B the stimulation signal is provided, and the polarities of the electrodes, based on signals from processor 30.

Figure 3:
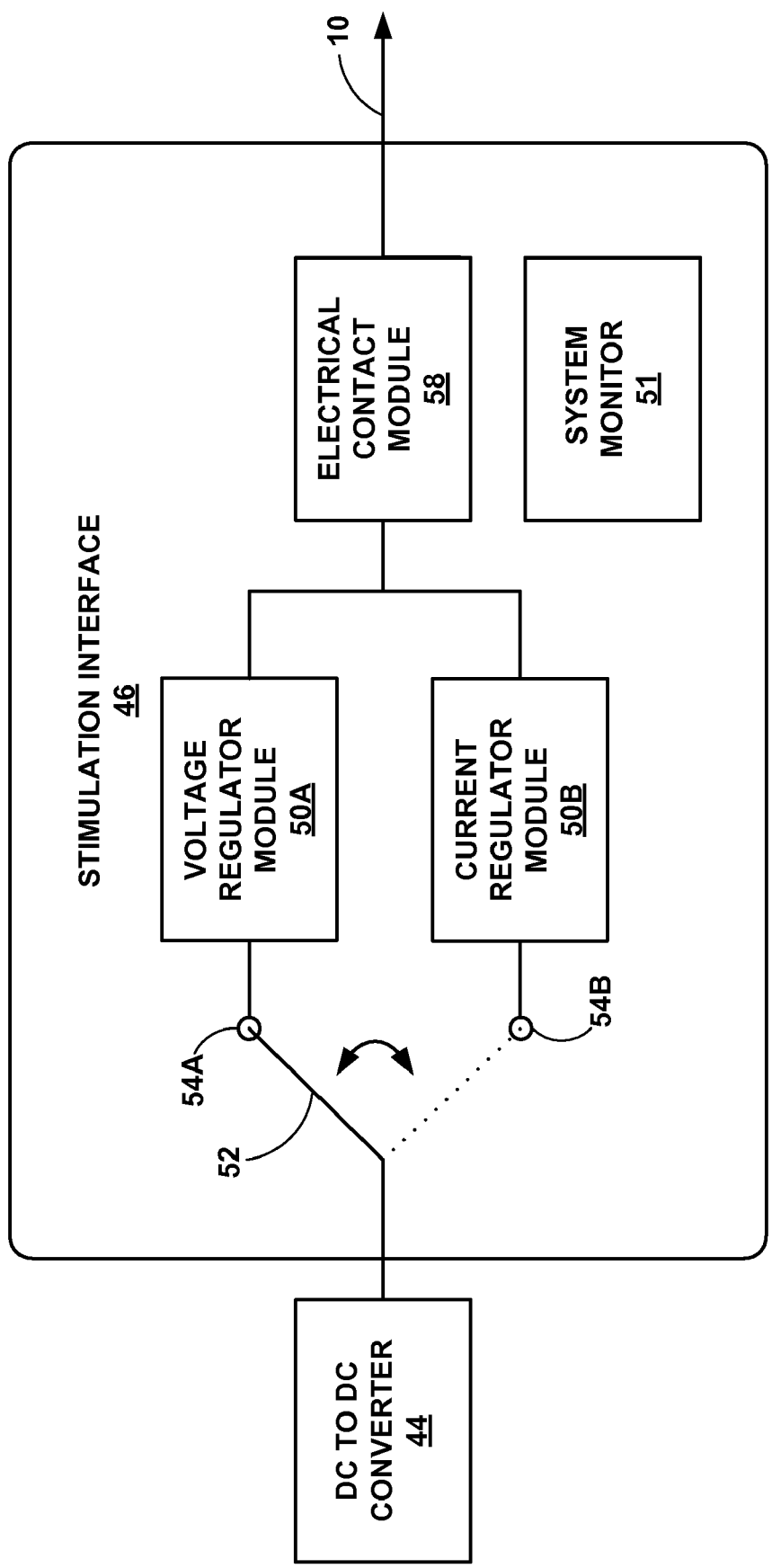
FIG. 3 is a block diagram illustrating various components of an example stimulation interface.

FIG. 3 is a block diagram illustrating various components of stimulation interface 46 according to one example embodiment. In the example illustrated in FIG. 3, stimulation interface 46 includes voltage regulator module 50A, current regulator module 50B, system monitor 51, and electrical contact module 58. Voltage regulator module 50A may include, for example, a voltage regulator that outputs a substantially constant voltage at a programmable value, and current regulator module 50B may include, for example, a current regulator that outputs a substantially constant current at a programmable value.

In the illustrated embodiment, stimulation interface 46 is selectively, e.g., based on a signal from processor 30, able to deliver either constant voltage or constant current stimulation pulses to patient 6 using voltage regulator module 50A or current regulator module 50B, respectively. However, the invention is not limited to embodiments in which both constant voltage and constant current pulses are available. Other embodiments may provide only constant voltage pulses, or only constant current pulses. Furthermore, as indicated above, the invention is not limited to embodiments in which stimulation is in the form of pulses.

In the example embodiment illustrated by FIG. 3, when therapy is delivered to patient 6 using constant voltage mode, processor 30 may actuate switch 52 to connect the output of DC to DC converter 44 to node 54A, which connects to voltage regulator module 50A. In this manner, the output of voltage regulator module 50A, a constant voltage at the amplitude specified by a stimulation program, is output to lead 10 via electrical contact module 58.

When stimulation is delivered to patient 6 using constant current mode, DC to DC converter 44 is coupled to current regulator module 50B via switch 52 as controlled by processor 30. When constant current stimulation is delivered to patient 6, processor 30 may actuate switch 52 to connect the output of DC to DC converter 44 to node 54B of current regulator module 50B. Current regulator module 50B will output a constant current to lead 10 via electrical contact module 58, at an amplitude specified by a stimulation program. In this manner, one of regulator modules 50A and 50B (collectively "regulator modules 50") may be active (referred to as the "active regulator module 50"), e.g., connected to DC to DC converter 44, depending on whether medical device 4 is delivering constant voltage or constant current stimulation.

The voltage that DC to DC converter 44 inputs into the active regulator module 50 may be higher than the output voltage outputted by the active regulator module 50. The voltage drop across the active regulator module 50 may provide adequate "headroom" for the active regulator module 50 to maintain the desired output value. For example, each of regulator modules 50 may require a minimum voltage drop between its input and output to ensure proper operation. The minimum voltage drop may be referred to as the required headroom.

Electrical contact module 58 may include a plurality of switches that may be controlled by processor 30. Each of the switches within electrical contact module 58 may be coupled to a conductor within lead 10 to allow processor 30 to control therapy delivery to a selected subset of electrodes according to an electrode configuration specified by a current stimulation program. However, the invention is not limited to embodiments that include an electrical contact module comprising a plurality of switches to selectively multiplex the output of an active regulator module 50 across a plurality of electrodes. In other embodiments, for example, each electrode of a lead 10 may be associated with a respective voltage and/or current source, e.g., voltage regulator module 50A and/or current regulator module 50B. Accordingly, in some embodiments, selection of electrodes and polarities by processor 30 according to an electrode configuration specified in a stimulation program may involve selection of a voltage or current source by the processor, instead of or in addition to switching the source across selected electrodes.

The active regulator module 50 may receive an input signal from capacitor module 44. Capacitor module 44 may include a plurality of capacitors and a switching array. The capacitors of capacitor module 44 may be configured into various configurations, including various charge and discharge configurations, using the switching array under control of processor 30. In this manner, processor 30 may control the charge and discharge configurations of the capacitors to produce a desired output of capacitor module 44, which is input into the active regulator module 50.

As one example, if a pair of capacitors is charged (e.g., configured in a charge configuration) across power source 34 in parallel and subsequently discharged (e.g., configured in a different discharge configuration) across a load in series, the output voltage of the capacitor pair will be double that of power source 34. In contrast, if a capacitor pair is charged across battery 34 in series and subsequently discharged across a load in parallel, the output voltage of the capacitor pair will be one half the voltage of power source 34. However, the example of capacitor pairs is used solely for purposes of illustration and is not intended to limit the invention. According to the invention, capacitor module 44 may include one or more capacitor pairs, capacitor triplets, capacitor octets, any other types of capacitor configurations, or any other number of capacitors.

In some embodiments, a maximum stack capacitor arrangement may be used to test if medical device 4 will be able to deliver stimulation according to a particular stimulation program given the present voltage level of power source 34. Maximum stack refers to a combination of charge and discharge configurations that result in the greatest possible multiple of the present power source voltage. The maximum stack arrangement allowed may vary based on power source type (e.g., non-rechargeable primary cell versus rechargeable) as well as stimulation mode (e.g., constant current versus constant voltage). When a maximum stack arrangement is used, the output of capacitor module 44 is as large as possible for the present power source voltage level, power source type, and stimulation mode.

The maximum stack arrangement of capacitor module 44 is used throughout this disclosure for purposes of example. However, the disclosure is not limited to embodiments in which DC to DC converter 44 is a capacitor module. More generally, DC to DC converter 44 may comprise any suitable type of DC to DC converter, such as an inductor-based charge pump, capacitor-based charge pump, and/or capacitor module. Consequentially, the maximum stack arrangement of capacitor module 44 may more generally be referred to as the maximum output configuration of DC to DC converter 44. A maximum output configuration may generally refer to a configuration of DC to DC converter 44 that supplies that highest voltage output, i.e., the greatest voltage boost. When a maximum output configuration is used, the output of DC to DC converter 44 is as large as possible for the present power source voltage level, power source type, and stimulation mode. The maximum output configuration is also used for purposes of example. As described in further detail with respect to FIGS. 8A and 8B, the invention is applicable to other output configurations selected by processor 30.

System monitor 51 may detect whether medical device 4 is able to deliver stimulation according to a present program. System monitor 51 may be coupled to regulator modules 50, and detect whether medical device 4 is able to deliver stimulation according to the present program by detecting out of regulation conditions. In other embodiments, system monitor 51 may be coupled to one or more of processor 30, regulator modules 50, and electrical contact module 58. System monitor 51 may measure a value of an electrical parameter within signal generator 40, such as a voltage, to detect whether medical device 4 is able to deliver stimulation according to the present program.

As one example, system monitor 51 may measure the voltage input into the active regulator module 50, and processor may compare the measured voltage to a threshold voltage. The threshold voltage may represent a minimum input voltage necessary to produce a stimulation signal according to the present program. As another example, when voltage regulator module 50A is active to deliver constant voltage stimulation, system monitor 51 may measure a voltage output of voltage regulator module 50A. Also, when current regulator module 50B is active to deliver constant current stimulation, system monitor 51 may measure a voltage output of current regulator module 50B. In this manner, system monitor 51 and processor 30 may detect if the active regulator module 50, e.g., voltage regulator module 50A if medical device 4 is delivering constant voltage stimulation or current regulator module 50B if medical device 4 is delivering constant current stimulation, is unable to produce an output signal that will support the presently selected stimulation program.

System monitor 51 may additionally or alternatively measure a voltage drop across the active regulator module 50, and processor 30 may detect whether there is sufficient headroom based on the measured voltage drop. Headroom refers to the voltage difference between the input of the active regulator module 50 and the output of the active regulator module 50. If the headroom is insufficient, e.g., the voltage drop is below a threshold value, the active regulator module 50 may not be able to provide a stimulation signal with a constant amplitude at the value specified by the present program. For example, the amplitude of a stimulation pulse may droop over the duration of the pulse.

As will be described in further detail with respect to FIGS. 4 and 5, a maximum stack capacitor arrangement may also be used to test if medical device 4 will be able to deliver stimulation according to a particular stimulation program throughout the useable voltage range of power source 34. For example, when medical device 4 delivers stimulation using the maximum stack configuration of capacitor module 44, system monitor 51 may measure one or more electrical parameter values to determine whether medical device 4 will be able to provide the stimulation output specified by a particular program throughout a voltage range of power source 34. As one example, system monitor 51 may determine the voltage drop across the active regulator module 50, e.g., by measuring and comparing the input and output of the active regulator module 50 or directly measuring the voltage drop across the active regulator module 50. The determined voltage drop across the active regulator module 50 may be utilized to determine if medical device 4 will be able to deliver stimulation according to a particular stimulation program.

If processor 30 determines that medical device 4 is, or will be, unable to deliver stimulation according to the selected program based on a parameter measured by system monitor 51, processor 30 may report the determination over a telemetry channel via telemetry module 36. For example, if processor 30 detects an out of regulation condition based on an electrical parameter value measured by system monitor 51, processor 30 may report the out of regulation condition via telemetry module 36. In response to such a report, a user may wish to modify the stimulation program, e.g., decrease an amplitude, of the stimulation signal. In embodiments in which power source 34 is rechargeable, a user may wish to recharge power source 34 in response to such a report. The report may be provided to the user, e.g., clinician or patient, via one of programmers 20, 22, or another external device. In addition to an indication that the medical device is, or will be, unable to deliver therapy according to the program, the external device may also provide recommendations to the user about how to respond, e.g., decrease an intensity of stimulation, recharge the power source, or the like.

In some embodiments, when stimulation is initiated according to a new program, or an intensity of the stimulation signal is increased, e.g., the programmed amplitude is increased, processor 30 configures capacitor module 44 to the maximum stack arrangement for delivery of the stimulation. Delivering stimulation using a maximum stack arrangement at these times may allow system monitor 51 and processor 30 to detect if the medical device 4 will be able to effectively deliver stimulation conforming to the specified stimulation parameter values of the new, or newly modified program at the present power source voltage level and/or determine, e.g., predict, if medical device 4 will continue to be able to deliver the stimulation specified by the selected program as power source 34 depletes.

If the medical device is able to effectively deliver the specified stimulation when the maximum stack arrangement is used, processor 30 may reconfigure the capacitors of capacitor module 44 to the most efficient stack arrangement for the program. The most efficient stack arrangement for a given program may allow the input of the active regulator module 50 to be greater than, but as close as possible to, the sum of the desired output of the active regulator module 50 and the required headroom. Adjusting capacitor module 44 in this manner may prolong the life of power source 34. Due to the time required to identify the most efficient stack arrangement, it may not be necessary or practical to adjust capacitor module 44 if the program is transient. Instead, capacitor module 44 may be ramped down after no programming changes have been received by processor 30, e.g., via telemetry module 36, for a threshold period of time.

Figure 4:
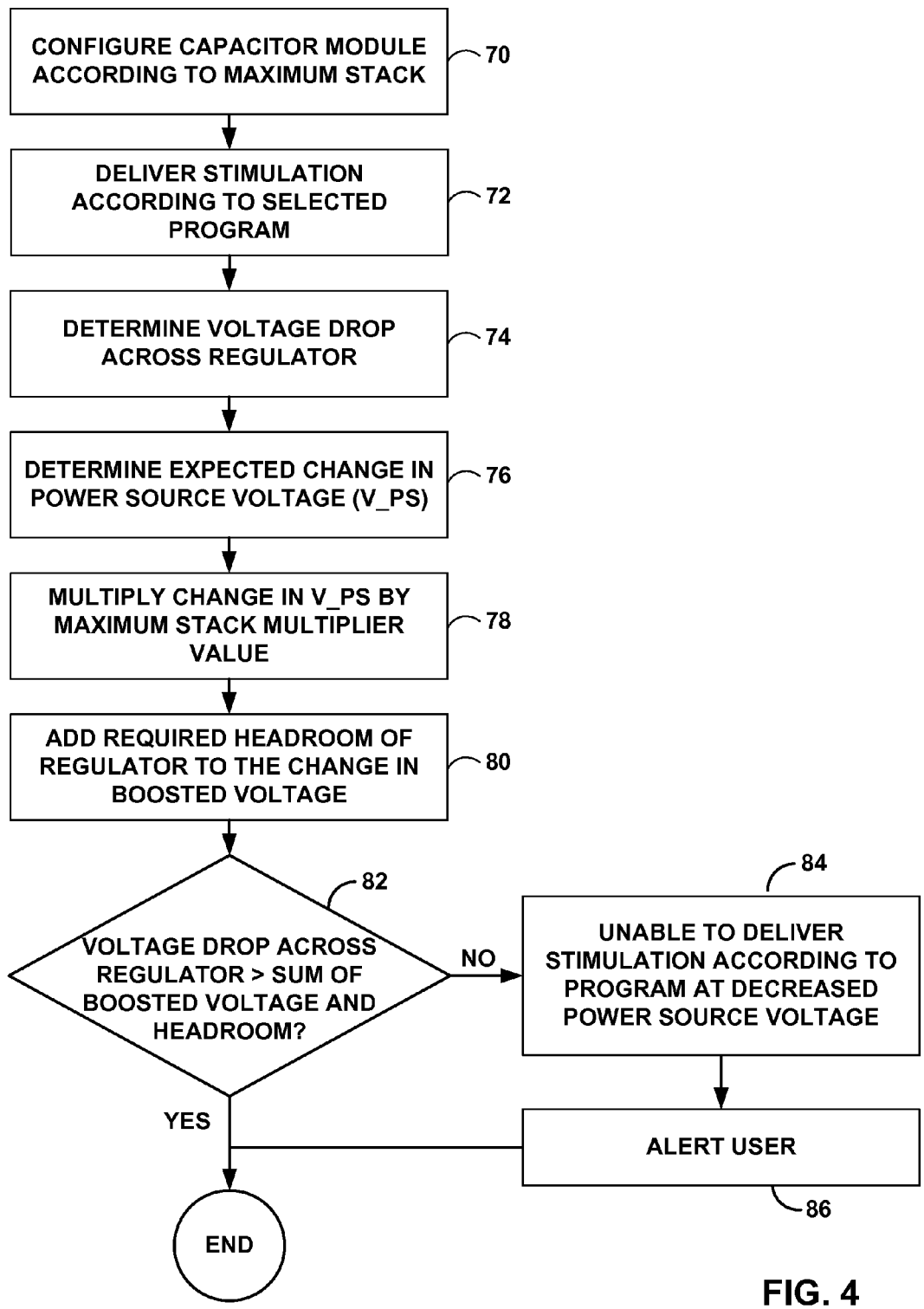
FIG. 4 is a flowchart illustrating an example method of determining whether a medical device will be able to deliver stimulation according to a program at a lower battery voltage level.

FIG. 4 is a flowchart illustrating an example method of determining whether medical device 4 will be able to deliver stimulation according to a program at a lower battery voltage level. Processor 30 configures capacitor module 44 into a maximum stack configuration (70) and controls delivery of stimulation according to the selected program (72). When a maximum stack arrangement is used, capacitor module 44 multiples the voltage provided by power source 34 by the largest multiplier that is available or allowed. The largest multiplier allowed may vary based on the type of power source 34 and/or the stimulation mode (e.g., constant current, constant voltage). For a given power source (e.g., power source 34) and stimulation mode, the largest multiplier allowed may be substantially constant. As a result, when the maximum stack configuration is used with power source 34 for the selected program, the output of capacitor module 44 is as large as possible for the present voltage level of power source 34. Consequentially, the voltage inputted into the active regulator module 50 of stimulation interface 46 is also as large as possible for the present voltage level of power source 34, since the output of capacitor module 44 is inputted into the active regulator module 50.

The active regulator module 50 outputs a voltage for delivery of stimulation according to the voltage or current amplitude specified by the selected therapy program. For example, if the selected program requires a constant voltage amplitude, voltage regulator module 50A may be active and output a voltage at the amplitude specified by the selected program. As another example, if the selected program requires a constant current amplitude, current regulator module 50B may be active and output a current at the amplitude specified by the selected program.

As previously described, the voltage supplied to the active regulator module 50 may be higher than the output voltage to provide adequate "headroom" for the active regulator module 50 to maintain the desired output voltage. For example, each of regulator modules 50 may require a minimum voltage drop between its input and output to ensure proper operation. This minimum voltage drop may be referred to as the required headroom. If the voltage supplied to the active regulator module 50 is greater than the sum of the desired output voltage and the required headroom, the voltage drop across the active regulator module 50 will be greater than the minimum voltage drop. This voltage drop across the active regulator module 50 equals the difference between the desired output voltage and the input voltage received from capacitor module 44.

Processor 30 and/or system monitor 51 may determine the voltage drop across the active regulator module 50 to aid in determining whether a lower voltage level of power source 34 may result in an out-of-regulation condition for the selected program (74). For example, system monitor 51 may measure both the voltage output from capacitor module 44 when capacitor module 44 is at maximum stack and the corresponding voltage output from the active regulator module 50. System monitor 51 and/or processor 30 may also calculate the difference between these two voltages. As another example, system monitor 51 may include a voltmeter that directly measures the voltage drop across the active regulator module 50.

Processor 30 may determine the expected change in voltage level of power source 34 as power source 34 depletes from its present voltage level to a lower voltage level (76). For example, processor 30 may control measurement of the present voltage level of power source 34. Additionally, memory 32 may store a value of the lower voltage level of power source 34. The lower voltage level of power source 34 may be the voltage level of power source 34 just prior to full depletion. For example, the lower voltage level of power source 34 may be a threshold voltage that defines a minimum voltage level of power source 34 below which therapy delivery by medical device 4 will cease. Processor 30 may calculate the difference between the present voltage level of power source 34 and the lower voltage level of power source 34. This difference in voltage levels may represent the expected change in the voltage level of power source 34 as power source 34 depletes from the present voltage level to the lower voltage level.

Processor 30 may multiply the expected change in the voltage level of power source 34 by the maximum stack multiplier value of capacitor array 44 (78). Processor 30 may calculate the maximum stack multiplier value by dividing the voltage output from capacitor module 44 when capacitor module 44 is at maximum stack, e.g., as measured by system monitor 51, by the present voltage level of power source 34. Alternatively, memory 32 may store the maximum stack multiplier value. In some embodiments, memory 32 stores values of multiple maximum stack multipliers that correspond to the various stimulation modes (e.g., constant current, constant voltage) allowed by medical device 4, and processor 30 retrieves the appropriate value based on the selected therapy program. The product of the expected change in the voltage level of power source 34 and the maximum stack multiplier value of capacitor array 44 may represent that expected decline in the maximum stack voltage outputted from capacitor module 44 as power source 34 reaches the lower voltage level. This product may be referred to as the change in boosted voltage.

Since a portion of the measured voltage drop across the active regulator module 50 is the required headroom of the active regulator module 50, processor 30 may add the value of the required headroom voltage to the change in boosted voltage to provide a basis for comparison between the change in boosted voltage and the value of the determined voltage drop across the active regulator module 50 (80). In order to deliver therapy according to the program at the lower voltage level of power source 34, the measured voltage drop must be greater than the sum of the required headroom and the change in boosted voltage. Since the voltage drop measured across the active regulator module 50 includes the required headroom (e.g., the minimum voltage drop required across the active regulator module 50 to ensure proper operation), the required headroom is added to the change in boosted voltage. In some embodiments, memory 32 may store the value of the required headroom for regulator modules 50.

The sum of the change in boosted voltage and required headroom is compared to the measured voltage drop across the active regulator module 50 (82). If the measured voltage drop across the active regulator module 50 is greater than the sum of the change in boosted voltage and required headroom, processor 30 determines that medical device 4 will be able to deliver stimulation according to the selected program at the lower voltage level of power source 34. However, if the measured voltage drop across the active regulator module 50 is less than the sum of the change in boosted voltage and required headroom, processor 30 determines that medical device 4 will be unable to deliver stimulation according to the selected program at the lower voltage level of power source 34 (84).

In response the determination that medical device 4 will not be able to correctly deliver the stimulation specified by the selected program at the lower battery voltage level, processor 30 may control telemetry module 36 to deliver an alert to a user, e.g., by controlling telemetry module 36 to transmit an indication or information to one or both of programming devices 20, 22, in the manner discussed above (86). As discussed above, a programming device may also provide recommendations to the user about how to avoid ineffective stimulation as power source 34 depletes, e.g., by suggesting a decrease in the intensity of stimulation, recharging power source 34 before its charge level reaches a specified lower power source voltage level, replacing power source 34 or medical device 4 when its voltage depletes to a certain value, or the like.

In some embodiments, processor 30 may reconfigure a minimum voltage level of power source 34 based on the determination that the medical device will be unable to deliver therapy according to the selected program at the lower battery voltage level. For example, processor 30 may inform a user of a programming device, e.g., programming device 20 or 22, or another external device that the medical device will be unable to deliver therapy according to the selected program at a lower battery voltage level via telemetry module 36. In addition to the indication that the medical device will be unable to deliver therapy according to the selected program at the lower power source voltage level, the external device may provide recommendations to the user about how to respond, e.g., decrease an intensity of stimulation, recharge the power source more frequently, or the like. In addition or instead of such recommendations, the external device may suggest reconfiguring the minimum voltage level of power source 34, such that power source 34 is replaced or recharged prior to reaching the lower power source voltage level. As described in further detail with respect to FIG. 7, in embodiments in which power source 34 is rechargeable, the external device may display a recharge frequency necessary to prevent the selected program from falling out of regulation.

FIG. 4 illustrates one example method of determining whether medical device 4 will be able to deliver stimulation according to a program at a lower battery voltage level. Other embodiments may include various modifications to the method illustrated in FIG. 4. For example, rather than adding the value of the required headroom to the change in the boosted voltage, processor 30 may subtract the required headroom value from the determined voltage drop across the active regulator module 50. Subtracting the required headroom from the determined voltage drop may yield the amount of excess voltage inputted into the active regulator module 50 above the amount required to produce the desired output and operate the active regulator module 50. In this manner, the difference between the determined voltage drop across the active regulator module 50 and the required headroom may yield the amount that the voltage input into the active regulator module 50 may decrease without compromising the ability of the active regulator module 50 to produce the desired outcome. This amount may be directly compared to the expected change in boosted voltage. The expected change in boosted voltage equals the expected decrease in the voltage input into the active regulator module 50, since the output of capacitor module 44 is inputted into the active regulator module 50.

Figure 5:
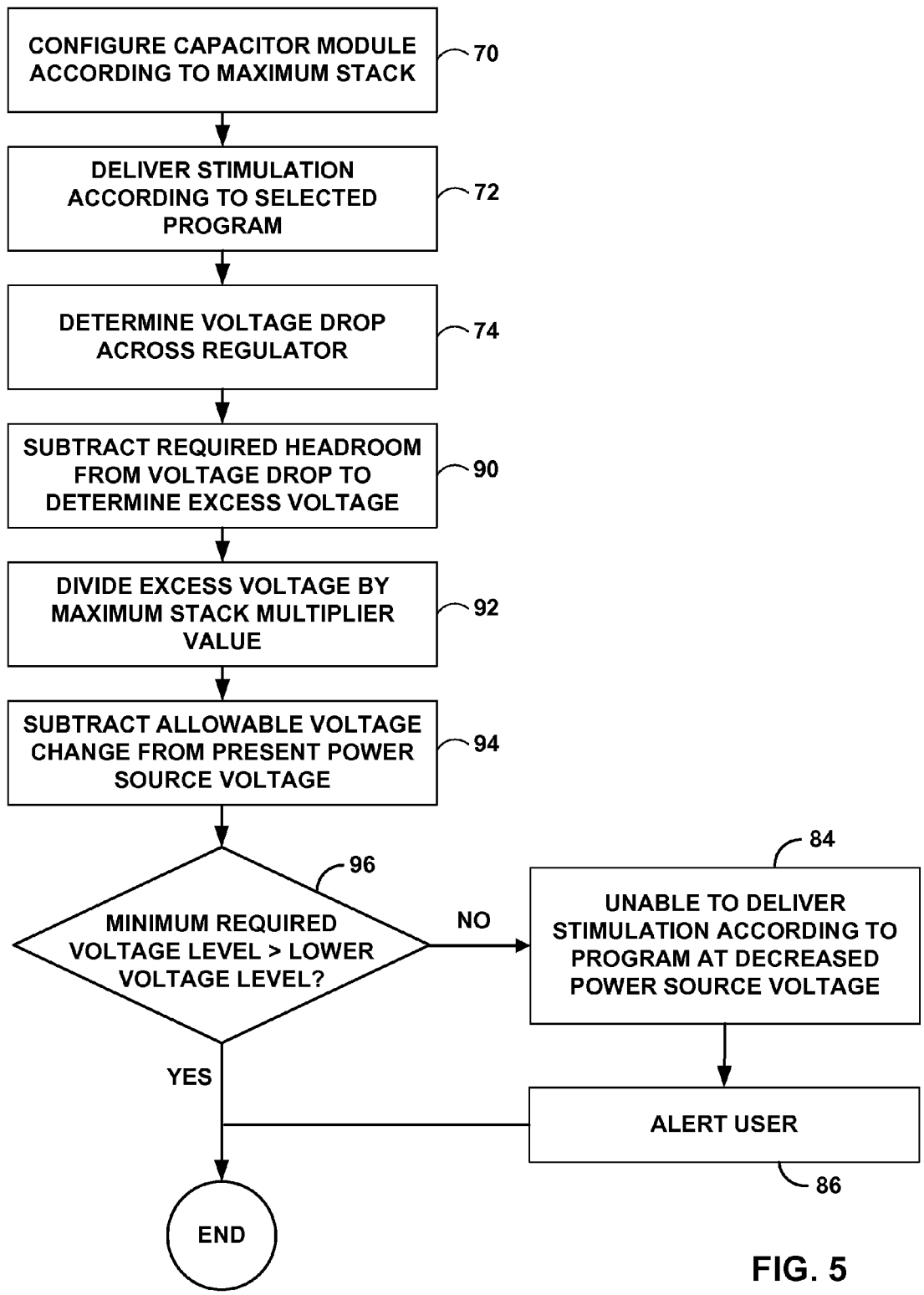
FIG. 5 is a flowchart illustrating another example method of determining whether a medical device will be able to deliver stimulation according to a program at a lower battery voltage level.

FIG. 5 is a flowchart illustrating another example method of determining whether medical device 4 will be able to deliver stimulation according to a program at a lower battery voltage level. As described with respect to FIG. 4, processor 30 configures capacitor module 44 into a maximum stack configuration (70) and controls stimulation delivery according to the selected program (72). Additionally, system monitor 51 and/or processor 30 determines the voltage drop across the active regulator module 50 (74).

Processor 30 may subtract the required headroom of the active regulator module 50 from the determined voltage drop value (90). In some embodiments, memory 32 may store the value of the required headroom for regulator modules 50. As previously described, subtracting the required headroom from the determined voltage drop value may yield the excess voltage inputted into the active regulator module 50 above the amount required to produce the desired output and operate the active regulator module 50. In this manner, the difference between the value of the determined voltage drop across the active regulator module 50 and the required headroom may yield the amount that the voltage input into the active regulator module 50 may decrease without compromising the ability of the active regulator module 50 to produce the desired outcome.

Processor 30 may also divide the calculated excess voltage value by the maximum stack multiplier value (92). As described previously, processor 30 may calculate the maximum stack multiplier value by dividing the voltage output from capacitor module 44 when capacitor module 44 is at maximum stack, e.g., as measured by system monitor 51, by the present voltage level of power source 34. Alternatively, memory 32 may store the maximum stack multiplier value. In some embodiments, memory 32 stores values of multiple maximum stack multipliers that correspond to the various stimulation modes (e.g., constant current, constant voltage) allowed by medical device 4, and processor 30 retrieves the appropriate value based on the selected therapy program.

Dividing the calculated excess voltage value by the maximum stack multiplier value may yield the maximum amount that the voltage of power source 34 may decrease without compromising the ability of the active regulator module 50 to produce the desired outcome according to the selected stimulation program. Therefore, this calculated change in the voltage level of power source 34 may be referred to as the allowable change in the voltage level of power source 34, since it defines a maximum threshold for the change in the voltage level of power source 34, above which the active regulator module 50 may be unable to produce the desired output according to the selected stimulation program. The allowable change in the voltage level of power source 34 may be subtracted from the present voltage level of power source 34 to yield the minimum voltage level of power source 34 necessary to ensure the active regulator module 50 will be able to produce the desired output according to the selected therapy program (94). As described previously, processor 30 may control measurement of the present voltage level of power source 34.

The minimum required voltage level of power source 34 may be compared to the lower voltage level of power source 34 (96). As previously described, memory 32 may store a value of the lower voltage level of power source 34. The lower voltage level of power source 34 may be the voltage level of power source 34 just prior to full depletion. For example, the lower voltage level of power source 34 may be a threshold voltage that defines a minimum voltage level of power source 34 below which therapy delivery by medical device 4 will cease.

If the lower voltage level of power source 34 is greater than the minimum required voltage level of power source 34, processor 30 determines that medical device 4 will be able to deliver stimulation according to the selected program at the lower voltage level of power source 34. However, if the lower voltage level of power source 34 is less than the minimum required voltage level of power source 34, processor 30 determines that medical device 4 will be unable to deliver stimulation according to the selected program at the lower voltage level of power source 34 (84).

In response to the determination that medical device 4 will not be able to correctly deliver the stimulation specified by the selected program at the lower battery voltage level, processor 30 may control telemetry module 36 to deliver an alert to a user, e.g., by controlling telemetry module 36 to transmit an indication or information to one or both of programming devices 20, 22, in the manner discussed above (86). As discussed above, programming device may also provide recommendations to the user about how to avoid ineffective stimulation as power source 34 depletes, e.g., by suggesting a decrease in the intensity of stimulation, recharging power source 34 before its charge level reaches a specified lower power source voltage level (e.g., the calculated minimum required voltage level), replacing power source 34 or medical device 4 when its voltage depletes to a certain value, or the like.

A programming device, e.g., programming device 20 or 22, or another external device may suggest reconfiguring the minimum voltage level of power source 34, such that power source 34 is replaced or recharged prior to reaching the lower power source voltage level. In some examples, the medical device may automatically configure the minimum voltage level of power source 34 in response to the determination that the medical device will be unable to deliver therapy according to the selected program. As described in further detail with respect to FIG. 7, in embodiments in which power source 34 is rechargeable, the external device may display a recharge frequency necessary to prevent the selected program from falling out of regulation, or reconfigure a display of the remaining charge of the power source, based on the reconfigured minimum voltage.

In some embodiments of the invention, the analysis to determine whether medical device 4 is, or will be, unable to deliver stimulation according to the selected program may be performed during a programming session by a clinician, e.g., using clinician programmer 20. The analysis may be performed during testing of new programs or modified programs during such a programming session. Based on the results of such analysis, the clinician may choose programs that medical device 4 will be able to support throughout the useable life of power source 34.

The delivery of ineffective stimulation may be prevented by determining whether a medical device will continue to be able to deliver stimulation as specified by a stimulation program as power source 34 depletes. This may be particularly important for patients receiving stimulation for movement disorders. Some of these patients may become physically disabled if the stimulation intensity is less than is necessary for effective reduction of movement disorder symptoms, making it difficult to correct the situation. If stimulation stops working properly for a patient receiving pain therapy, the patient may be able to alert the clinician, recharge the power source, etc. In contrast, if stimulation stops working properly for a movement disorder patient, the patient may be unable to do so. Additionally, a patient receiving pain therapy may feel tingling sensations during stimulation delivery and notice when the stimulation is interrupted. A patient receiving DBS to treat a movement disorder may not notice that stimulation has been interrupted until symptoms occur, at which point the patient may be unable to correct the situation.

As previously described, in some embodiments, each electrode of a lead 10 may be associated with a respective voltage or current source, e.g., voltage regulator and/or current regulator. Accordingly, in some embodiments, selection of electrodes and polarities by processor 30 according to an electrode configuration specified in a stimulation program may involve selection of a voltage or current source by the processor, instead of or in addition to switching the source across selected electrodes. For example, in embodiments in which medical device 4 may deliver either constant voltage or constant current stimulation, voltage regulator module 50A may include a voltage regulator for each electrode of a lead 10, and current regulator module 50B may provide a current regulator for each electrode of a lead 10.

Figure 6:
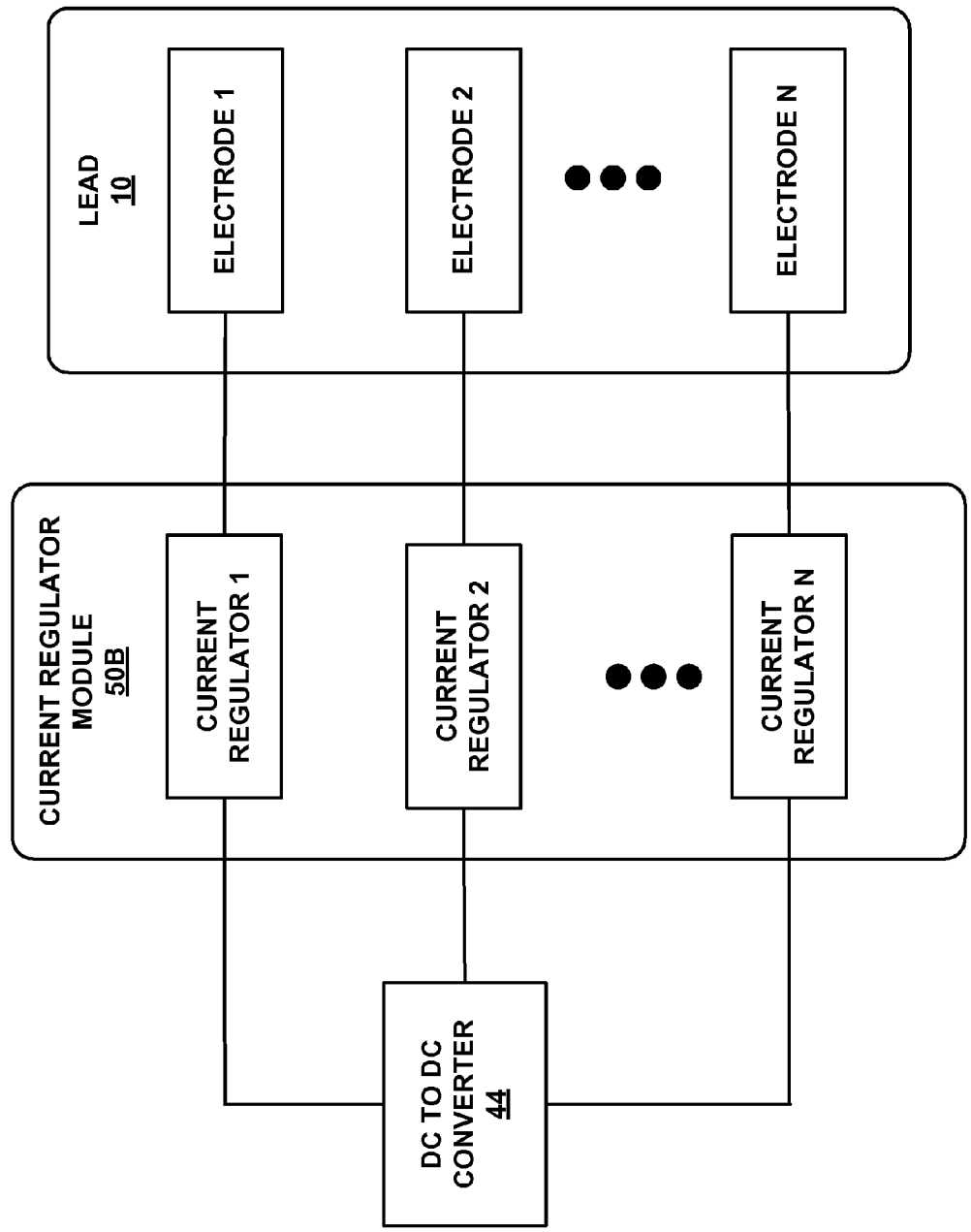
FIG. 6 illustrates an example configuration of a stimulation interface in which each electrode of a lead is associated with a respective current regulator.

FIG. 6 illustrates an example configuration in which each electrode of lead 10 is associated with a respective current regulator to deliver stimulation at a constant current. Lead 10 may include any number of electrodes, and regulator module 50B may include a regulator for each electrode such that one regulator is associated with each electrode of lead 10.

In the example embodiment illustrated by FIG. 6, therapy is delivered to patient 6 at a constant current. However, this disclosure is not limited to using multiple current sources to deliver therapy at a constant current. In other embodiments, each electrode of a lead 10 may be associated with a respective voltage and/or current source, e.g., voltage regulator and/or current regulator, to deliver therapy at a constant voltage and/or constant current.

In the constant current stimulation embodiment illustrated in FIG. 6, the regulators of regulator module 50B may each output a constant current to lead 10 at an amplitude specified by a stimulation program, based on a digital input from processor 30. For example, processor 30 may specify which electrodes of lead 10 will be activated to deliver stimulation and also the polarities of the active electrodes. Additionally, when therapy is delivered at a constant current, each of the active regulators of regulator module 50B may output a non-zero voltage. For example, a first regulator of regulator module 50B may output a voltage at 12 V and a second regulator of module 50B may output a voltage at 2 V. The 12 V output may deliver a specified constant current to an electrode of lead 10 that is configured as an anode. The 2 V output may deliver a specified constant current to an electrode of lead 10 that is configured as a cathode.

In contrast, in some embodiments, when therapy is delivered at a constant voltage and voltage regulator module 50A includes multiple voltage regulators, the active regulators of 50A may either input voltage values of approximately 0 V or voltage values approximately equal to the voltage specified by the selected stimulation program. For example, a regulator of regulator module 50A that corresponds to an electrode configured as a cathode may output a negative voltage according to an amplitude specified by the selected program, and a regulator that corresponds to an electrode configured as an anode may be connected to ground and, therefore, output a voltage of approximately 0 V. Since each negative cathode voltage value may be associated with an anode voltage value of approximately 0 V, the overall output of regulator module 50A may accurately reflect the total amount of voltage output from regulator module 50A.

With constant current mode, the voltage values outputted from regulators of regulator module 50B associated with anodes may be nonzero. Additionally, the voltage values outputted from the regulators of regulator module 50B may change as the voltage level of power source 34 decreases. Using the example presented above, a regulator associated with an anode may output 12 V, and a regulator associated with a cathode may output 2 V. However, as the voltage level of power source 34 decreases, processor 30 may realign the regulators such that, for example, the regulator associated with the anode outputs 11 V, and the regulator associated with the cathode outputs 1 V. Since the voltage difference between the anode and cathode is the same, the same therapy may be delivered using the 11 V and 1 V outputs or the 12 V and 2 V outputs. Since the voltage values output from the regulators associated with anodes and cathodes may fluctuate as long as the voltage difference between the regulators remains constant, the voltage difference between the regulators associated with an anode and cathode may be used to calculate the output of regulator module 50B rather than the sum of the voltage outputs.

Since, with constant current mode, the output voltages of the individual regulators of regulator module 50B that are configured as anodes may be nonzero, the overall voltage output of regulator module 50B may not provide enough information regarding the total amount of voltage output from regulator module 50B. With constant current mode, instead of using the output of regulator module 50B to determine the voltage drop across regulator module 50B, the voltage difference between regulators associated with an anode and cathode may be used.

As one example, system monitor 51 may identify the regulator that outputs the largest voltage and the regulator that outputs the smallest voltage, e.g., the regulators corresponding to the greatest anode and smallest cathode. Since the greatest voltage difference between an anode and cathode requires the most voltage from power source 34, these regulators may fall out of regulation first, e.g., at a higher voltage level of power source 34 than regulators corresponding to smaller anodes and larger cathodes that result in a smaller voltage difference between anode and cathode. The difference between the voltage values output from the regulators corresponding to the largest cathode and smallest anode may be compared to the voltage input into regulator module 50B to determine the voltage drop across regulator module 50B.

To identify the regulators corresponding to the largest anode and smallest cathode, system monitor 51 may measure the voltage output of each regulator of regulator module 50B with respect to a common reference, e.g., ground. The common reference may be the same reference used to measure the overall voltage input into regulator module 50B. In cases where a common reference is not available for the outputs of the plurality of regulators, system monitor 51 may measure all of the active regulators with respect to each other. This type of factorial screening may allow system monitor 51 to identify the regulators corresponding to the largest anode and smallest cathode by identifying the two regulators with the greatest difference between their output voltages. This voltage difference may be compared to the voltage input into regulator module 50B to determine the voltage drop across regulator module 50B.

As previously stated, when regulator module 50B does not permit direct measurement of the voltages output from its individual regulators, system monitor 51 may use factorial screening to measure the outputs of all of the active regulators with respect to each other. Which regulators are active may depend on which program is activated. More specifically, each program includes an electrode configuration that specifies the particular electrodes within an electrode set are to be used to deliver the pulses or continuous-time signal, and the polarities of the selected electrodes. For a given program, only the regulators corresponding to the electrodes used to deliver the pulses or continuous-time signal may be activated. Only the activated regulators need to be screened.

When nonzero voltages are output from both the regulators of regulator module 50B configured as anodes and the regulators of regulator module 50B configured as cathodes, determining the difference between the voltage values output from the regulators corresponding to the largest cathode and smallest anode may provide information about the amount of voltage being output from regulator module 50B. As described with respect to FIGS. 4 and 5, the difference between the amount of voltage input into regulator module 50B and the amount of voltage output from regulator module 50B, e.g., the voltage drop across regulator module 50B, may be used to determine if the selected program will cause an out of regulation condition at a lower power source voltage level.

Figure 7:
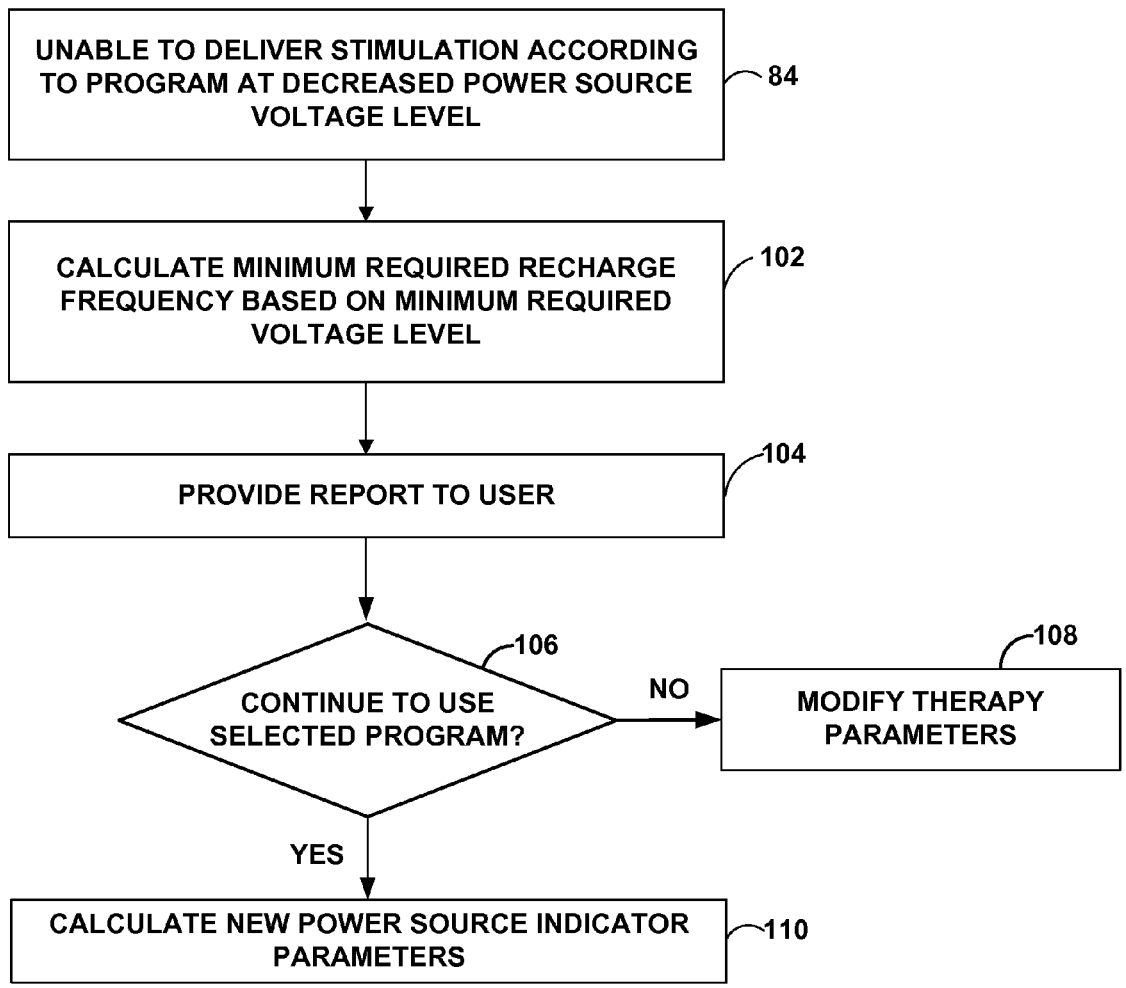
FIG. 7 is a flowchart illustrating an example method of reconfiguring a minimum voltage level of a power source.

FIG. 7 is a flow diagram illustrating an example method of reconfiguring a minimum voltage level of power source 34. Although FIG. 7 is primarily described with respect to embodiments in which power source 34 is rechargeable, in other embodiments, a minimum voltage level of a non-rechargeable power source may be reconfigured.

As described with respect to FIGS. 4 and 5, processor 30 determines that medical device 4 will be unable to deliver stimulation according to the selected program at the lower voltage level of power source 34 (84). Based on this determination, processor 30 or a processor of an external device, e.g., programmer 20 or 22, may calculate the minimum recharge frequency required to prevent the selected program from falling out of regulation (102). The minimum required recharge frequency may be based on the minimum voltage level of power source 34 necessary to ensure the active regulator module 50 will be able to produce the desired output according to the selected therapy program, i.e., the minimum required voltage level, as described with respect to FIG. 5. For example, the minimum required recharge frequency may be the recharge frequency required to prevent the voltage level of power source 34 from falling below the sum of the minimum required voltage level and a threshold value.

In embodiments in which power source 34 is non-rechargeable, processor 30 or a processor of an external device may calculate a modified power source replacement schedule. For example, processor 30 may calculate how much earlier power source 34 would need to be replaced if the selected therapy program were used for therapy delivery. The modified replacement schedule may be based on the minimum required voltage level of power source 34. For example, power source 34 may need to be replaced prior to depleting to the minimum required voltage level.

The external device, e.g., programmer 20 or 22, may display a report to a user specifying the minimum required recharge frequency (104). For example, processor 30 may control telemetry module 36 to provide the report to the external device. The report may also include an indication that the medical device may be unable to deliver stimulation according to selected program at the lower power source voltage level. In some embodiments, the report may provide recommendations to a user based on how much the minimum required recharge frequency for the selected program compares to the recharge frequency typically used when power source 34 is allowed to deplete to the lower power source voltage level. For example, if the minimum required recharge frequency for the selected program substantially varies from the recharge frequency typically used when power source 34 is allowed to deplete to the lower power source voltage level, the report may suggest decreasing the stimulation intensity instead of modifying the recharge frequency.

A user may decide whether to continue using the selected program (106). If the user does not chose to continue therapy delivery using the selected program, the therapy parameters may be modified (108). For example, a user may decrease the stimulation intensity of the selected program or select a new program, e.g., via programming device 20 or 22.

If the user decides to continue using the selected program for therapy delivery, the power source voltage level indicator parameters are reconfigured (110). Programming device 20 and/or programming device 22 may display an indicator of the present voltage level of power source 34. The power source voltage level indicator allows the user to determine when power source 34 requires recharging. The gauge of the power source voltage indicator may be rescaled to reflect the minimum required recharge frequency associated with the selected program.

In some embodiments, the power source voltage indicator includes marking to indicate that the power source voltage level is at a maximum, three fourths of the maximum, one half of the maximum, one fourth of the maximum, and a minimum. The minimum voltage level displayed on the gauge may be set, for example, to the minimum voltage level of power source 34 necessary to ensure the active regulator module 50 will be able to produce the desired output according to the selected therapy program. Likewise, the half and quarter markings may be recalculated to reflect the new minimum voltage level of power source 34.

Figure 8A:
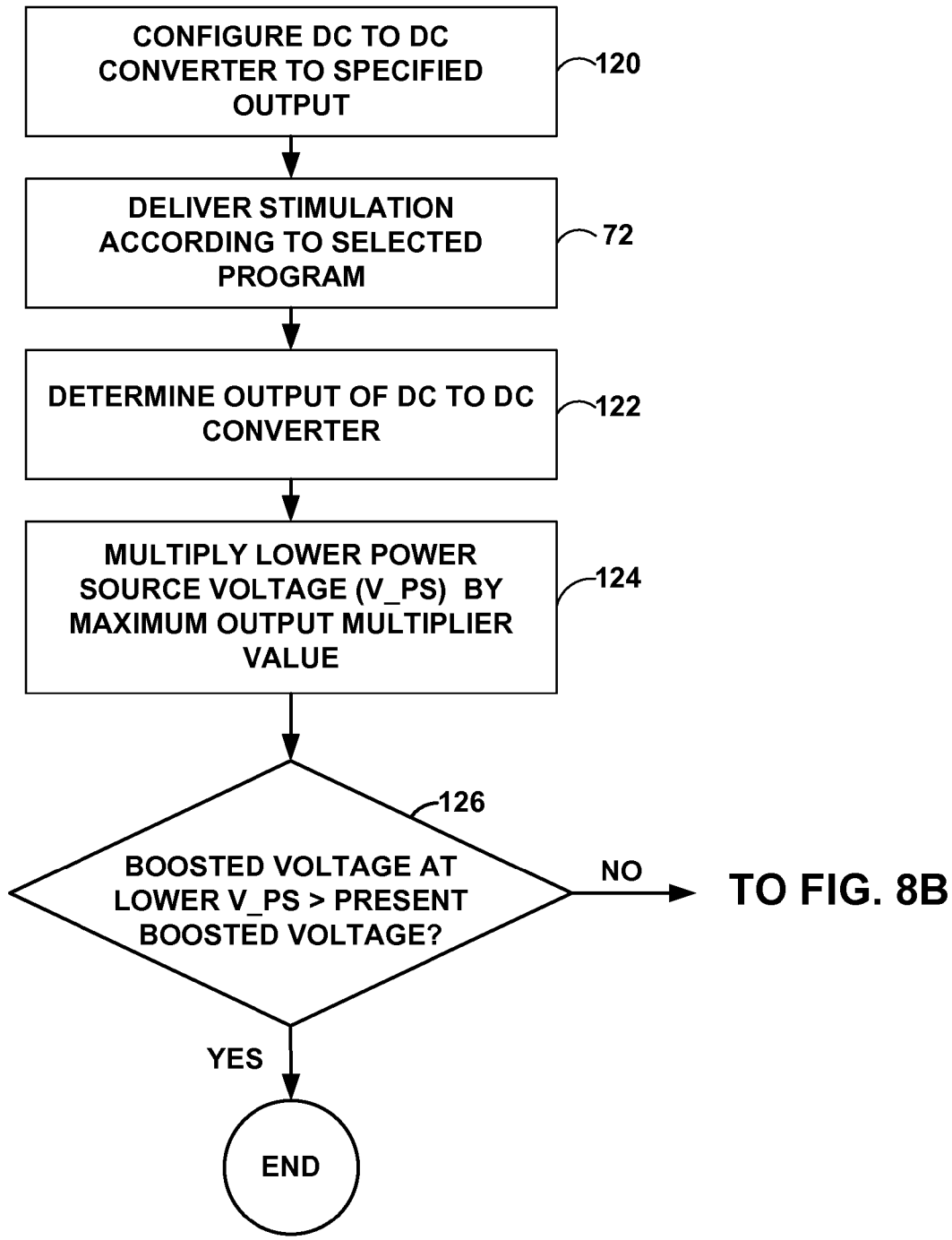
FIGS. 8A and 8B are flowcharts illustrating another example method of determining whether a medical device will be able to deliver stimulation according to a program at a lower battery voltage level.
Figure 8B:
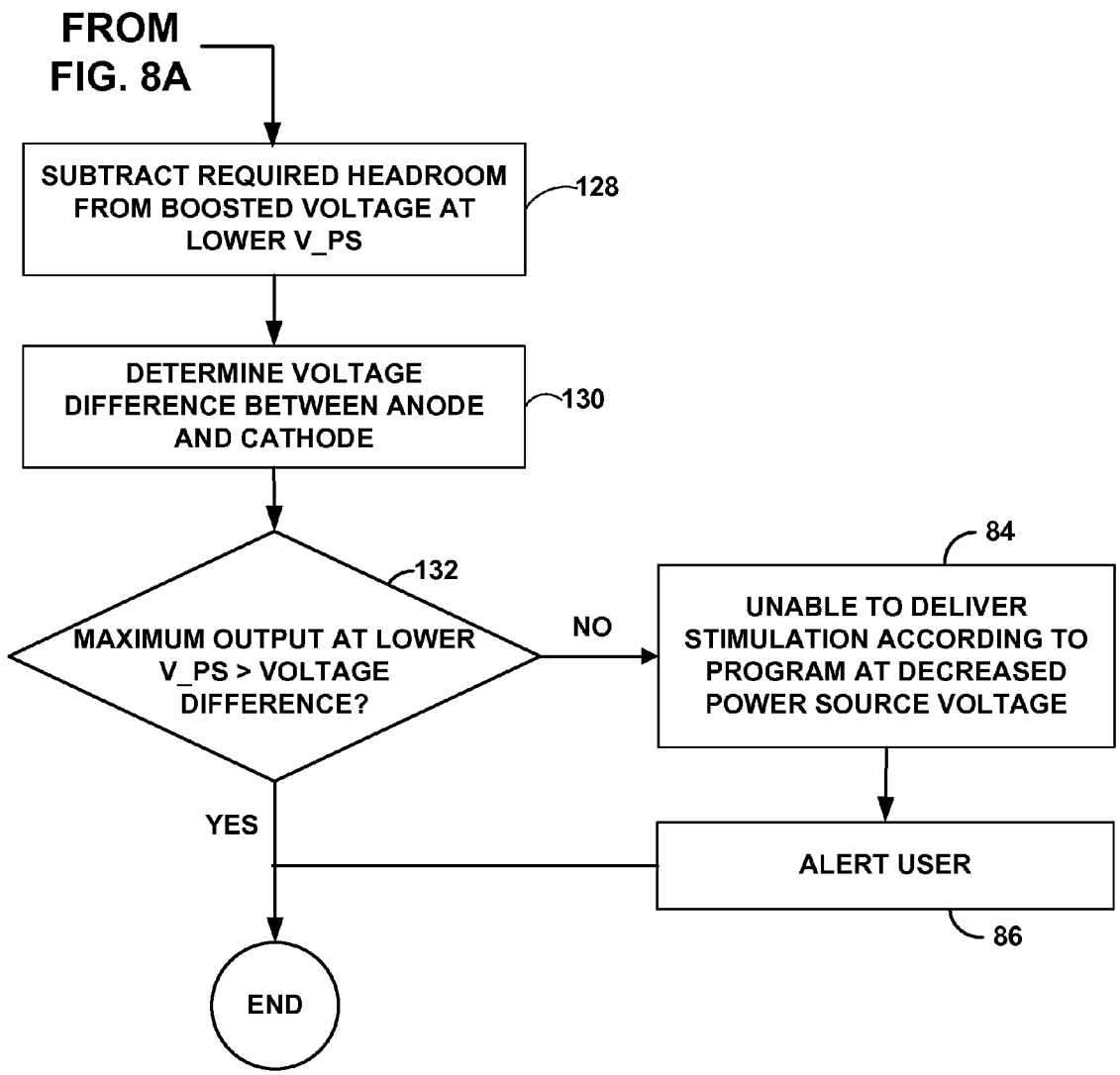

FIGS. 8A and 8B are flow diagrams illustrating another example method of determining whether a medical device will be able to deliver stimulation according to a program at a lower battery voltage level. Processor 30 configures DC to DC converter 44 into a specified output configuration, e.g., configures a capacitor module to a specified stack (120). The specified output configuration may be a configuration of DC to DC converter 44 less than the maximum level of boost available, e.g., a configuration of capacitor module 44 less than the maximum stack configuration. For example, the specified stack configuration may be the most efficient stack arrangement for the selected program. The most efficient stack arrangement for a given program may allow the input of the active regulator module 50 to be greater than, but as close as possible to, the sum of the desired output of the active regulator module 50 and the required headroom. More generally, the specified stack configuration may comprise a specified output configuration of any suitable type of DC to DC converter 44, such as an inductor-based charge pump, capacitor-based charge pump, and/or capacitor module.

Processor 30 controls medical device 4 to deliver stimulation according to the selected program (72) and determines the output of the DC to DC converter 44 at the specified stack configuration of capacitor module 44 and the present power source voltage level of power source 34 (122). Processor 30 also multiplies the lower power source voltage level by the maximum stack multiplier value of capacitor module 44 to yield the maximum output of capacitor module 44 at the lower power source voltage level (124). As previously described, the lower voltage level of power source 34 may be the voltage level of power source 34 just prior to full depletion. For example, the lower voltage level of power source 34 may be a threshold voltage that defines a minimum voltage level of power source 34 below which therapy delivery by medical device 4 will cease.

Processor 30 compares the maximum output of capacitor module 44 at the lower power source voltage level to the present output of capacitor module 44 at the specified stack configuration and the present power source voltage level (126). If the maximum output of capacitor module 44 at the lower power source voltage level is greater than the present output of capacitor module 44, medical device 4 will be able to deliver therapy according to the selected program at the lower power source voltage level of power source 34. Since medical device 4 may deliver therapy at the present output of capacitor module 44, and the maximum output of capacitor 44 does not fall below the present output of capacitor module 44 as medical device 4 reaches the lower power source voltage level, medical device 4 will be able to deliver therapy at the lower power source voltage level.

Referring to FIG. 8B, if the maximum output of capacitor module 44 at the lower power source voltage level is less than the present output of capacitor module 44, processor 30 subtracts the required headroom of the active regulator module 50 from the maximum output of capacitor module 44 at the lower power source voltage level to yield the maximum output that the active regulator module 50 may support (128).

Processor 30 also determines the greatest voltage difference between two regulators of the active regulator module 50, e.g., the greatest voltage difference between a regulator configured as an anode and a regulator configured as a cathode (130). Processor 30 compares the maximum voltage difference between two regulators of the active regulator module 50 to the maximum output that the active regulator module 50 may support at the lower power source voltage level (132). If the maximum output that the active regulator module 50 may support at the lower power source voltage level is greater than the maximum voltage difference between two regulators of the active regulator module 50, medical device 4 will be able to deliver therapy according to the selected program at the lower power source voltage level of power source 34.

If the maximum output that the active regulator module 50 may support at the lower power source voltage level is less than the maximum voltage difference between two regulators of the active regulator module 50, processor 30 determines that medical device 4 will be unable to deliver stimulation according to the selected program at the lower voltage level of power source 34 (84). In response to the determination that medical device 4 will not be able to correctly deliver the stimulation specified by the selected program at the lower battery voltage level, processor 30 may control telemetry module 36 to deliver an alert to a user, e.g., by controlling telemetry module 36 to transmit an indication or information to one or both of programming devices 20, 22, in the manner discussed above (86). As discussed above, programming device may also provide recommendations to the user about how to avoid ineffective stimulation as power source 34 depletes, e.g., by suggesting a decrease in the intensity of stimulation, recharging power source 34 before its charge level reaches a specified lower power source voltage level (e.g., the calculated minimum required voltage level), replacing power source 34 or medical device 4 when its voltage depletes to a certain value, or the like.

Any of the methods of determining whether medical device 4 will be able to support a selected stimulation program at a lower power source voltage level described herein, including the example methods described with respect to FIGS. 4, 5, 8A, and 8B, may account for a margin of error. The margin of error may help ensure that medical device 4 stays in regulation even with slight variances in load impedance, lead impedance, and/or power source impedances. For example, processor 30 may base its determinations of whether medical device 4 will be able to support a selected stimulation program at a lower power source voltage level based on a power source voltage some higher than the voltage level of power source 34 that triggers medical device 4 to cease therapy delivery, e.g., ten percent higher than the voltage level of power source 34 that triggers medical device 4 to cease therapy delivery. A ten percent threshold value is listed for purposes of example. Other threshold values are also contemplated.

Various embodiments of the invention have been described. One of ordinary skill in the art will understand that various modifications may be made to the described embodiments without departing from the scope of the claimed invention. For example, although described with reference to embodiments in which a voltage or current source for delivery of stimulation includes a voltage regulator, the invention is not so limited. Other embodiments may additionally or alternatively include a current regulator. These and other embodiments are within the scope of the following claims.

The invention claimed is:

1. A medical device comprising:
   a power source at a present power source voltage level;
   a signal generator that generates electrical stimulation, wherein the signal generator comprises:
   a DC to DC converter coupled to the power source; and
   a regulator module coupled to the DC to DC converter; and a processor that controls the signal generator to configure the DC to DC converter in a specified output configuration and deliver stimulation according to a program while at the specified output configuration, determines a value of a voltage drop across the regulator module during the delivery of electrical stimulation according to the program, and determines whether the medical device will be able to deliver stimulation according to the program at a power source voltage level lower than the present voltage level of the power source based on the determined value of the voltage drop.

2. The medical device of claim 1, further comprising a transceiver that is configured to communicate with a programming device that is located external to the medical device, wherein the processor sends an indication via the transceiver of whether the medical device will be able to deliver stimulation according to the program at the lower power source voltage level based on the determined value of the voltage drop.

3. The medical device of claim 2, wherein the indication comprises an indication that the medical device is not able to deliver electrical stimulation according to the program at the lower power source voltage level, wherein the power source comprises a rechargeable power source, and wherein the indication further comprises a minimum recharge frequency required for the program.

4. The medical device of claim 3, wherein the processor rescales a gauge of a power source voltage level indicator based on the minimum recharge frequency required for the program.

5. The medical device of claim 2, wherein the indication comprises an indication that the medical device is not able to deliver electrical stimulation according to the program at the lower power source voltage level, wherein the power source comprises a non-rechargeable power source, and wherein the indication further comprises a modified power source replacement schedule required for the program.

6. The medical device of claim 2, wherein the regulator module comprises a plurality of regulators, and wherein the processor determines a value of a voltage drop across the regulator module by measuring a first output of a first regulator configured as a cathode, measuring a second output of a second regulator configured as an anode, and calculating a difference between the first output and the second output.

7. The medical device of claim 1, wherein the medical device comprises an implantable medical device.

8. The medical device of claim 1, wherein the power source comprises a battery.

9. The medical device of claim 1, wherein the power source is rechargeable.

10. The medical device of claim 1, wherein the processor measures the present power source voltage level.

11. The medical device of claim 1, wherein the lower power source voltage level comprises a minimum threshold voltage of the power source below which therapy delivery by the medical device will cease.

12. The medical device of claim 1, wherein the processor calculates a minimum voltage level required to deliver stimulation according to the program based on the determined voltage drop value and compares the minimum required voltage level to the lower power source voltage level to determine whether the medical device will be able to deliver stimulation according to the program at the lower power source voltage level.

13. The medical device of claim 1, wherein the processor calculates an expected decrease in a level of voltage input into the regulator module as the present voltage level depletes to the lower voltage level and determines whether the medical device will be able to deliver stimulation according to the program at the lower power source voltage level based on the determined value of the voltage drop and the expected decrease in input voltage.

14. The medical device of claim 1, wherein the DC to DC converter comprises a capacitor module, the specified output configuration comprises a specified stack configuration, and delivering electrical stimulation comprises discharging the capacitor module through the regulator module.

15. The medical device of claim 1, wherein the specified output configuration comprises a maximum output configuration.

16. A medical device comprising:
means for configuring a DC to DC converter in a specified output configuration;
means for delivering electrical stimulation according to a program while at the specified output configuration;
means for determining a value of a voltage drop across a regulator module within the medical device while delivering the electrical stimulation according to the program; and
means for determining whether the medical device will be able to deliver stimulation according to the program at a power source voltage level lower than a present voltage level of a power source based on the determined value of the voltage drop.

17. A medical device comprising:
a power source at a present power source voltage level;
a signal generator that generates electrical stimulation, wherein the signal generator comprises:
a DC to DC converter coupled to the power source; and
a regulator module coupled to the DC to DC converter; and
a processor that controls the signal generator to configure the DC to DC converter in a specified output configuration and deliver stimulation according to a program while at the specified output configuration, determines a first output of the DC to DC converter at the specified output configuration and the present battery power source voltage level, determines a second output of the DC to DC converter at a maximum output configuration and a power source voltage level lower than the present voltage level of the power source, compares the first and second outputs, and determines whether the medical device will be able to deliver stimulation according to the program at the power source voltage level lower than the present voltage level of the power source based on the comparison.

18. The medical device of claim 17, wherein the processor determines that the medical device will be able to deliver stimulation according to the program when the second output is at least one of greater than or equal to the first output.

19. The medical device of claim 17, wherein, when the second output is less than the first output, the processor determines a voltage drop across the regulator module at the second output of the DC to DC converter at the maximum output configuration and the power source voltage level lower than the present voltage level of the power source, and determines whether the medical device will be able to deliver stimulation according to the program at the power source voltage level lower than the present voltage level of a power source based on the determined value of the voltage drop.

* * * * *